US00PP29822P2

(12) United States Plant Patent
Larsen

(10) Patent No.: US PP29,822 P2
(45) Date of Patent: Nov. 13, 2018

(54) MINIATURE ROSE PLANT NAMED 'QIR 1601'

(50) Latin Name: *Rosa hybrida*
Varietal Denomination: QIR 1601

(71) Applicant: Michael Larsen, Sabro (DK)

(72) Inventor: Michael Larsen, Sabro (DK)

(73) Assignee: Q-Genetics ApS, Sabro (DK)

( * ) Notice: Subject to any disclaimer, the term of this patent is extended or adjusted under 35 U.S.C. 154(b) by 0 days.

(21) Appl. No.: 15/731,448

(22) Filed: Jun. 12, 2017

(51) Int. Cl.
*A01H 5/02* (2018.01)

(52) U.S. Cl.
USPC ..... Plt./118

(58) Field of Classification Search
USPC ..... Plt./118, 125
CPC ..... A01H 5/0222
See application file for complete search history.

*Primary Examiner* — June Hwu
(74) *Attorney, Agent, or Firm* — C. A. Whealy

(57) ABSTRACT

A new and distinct cultivar of Rose plant named 'QIR 1601', characterized by its upright and mounding plant habit; strong lateral branches; dark green-colored leaflets; large intense yellow-colored flowers; flowers held upright on strong and erect peduncles; and good postproduction longevity.

3 Drawing Sheets

Botanical designation: *Rosa hybrida.*
Cultivar denomination: 'QIR 1601'.

BACKGROUND OF THE INVENTION

The present Invention relates to a new and distinct cultivar of Rose or *Rosa* plant, botanically known as *Rosa hybrida*, commercially used as a potted Rose plant and hereinafter referred to by the name 'QIR 1601'.

The new Rose plant is a product of a planned breeding program conducted by the Inventor in Odense, Denmark. The objective of the breeding program was to develop new uniform and healthy potted Rose varieties with attractive flower colors and excellent postproduction longevity.

The new Rose plant originated from a cross-pollination made by the Inventor in March, 2013 of *Rosa hybrida* 'Sunbeam', not patented, as the female, or seed, parent with a proprietary *Rosa hybrida* selection identified as code number 243, not patented, as the male, or pollen, parent. The new Rose plant was discovered and selected by the Inventor on May 19, 2014 as a single flowering plant within the progeny of the stated cross-pollination in a controlled greenhouse environment in Odense, Denmark.

Asexual reproduction of the new Rose plant by cuttings in a controlled greenhouse environment in Odense, Denmark since May, 2014 has shown that the unique features of this new Rose plant are stable and reproduced true to type in successive generations of asexual reproduction.

SUMMARY OF THE INVENTION

The following traits have been repeatedly observed and are determined to be the unique characteristics of 'QIR 1601'. These characteristics in combination distinguish 'QIR 1601' as a new and distinct Rose plant:

1. Upright and mounding plant habit.
2. Strong lateral branches.
3. Dark green-colored leaflets.
4. Large intense yellow-colored flowers.

5. Flowers held upright on strong and erect peduncles.
6. Good postproduction longevity.

Plants of the new Rose differ from plants of the female parent, 'Sunbeam', primarily in flower form as flowers of plants of 'Sunbeam' are flatter and not as recurved as flowers of the new Rose plant.

Plants of the new Rose differ from plants of the male parent selection primarily in flower color as flowers of plants of the male parent selection are yellow orange in color. In addition, plants of the new Rose are more freely flowering than plants of the male parent selection.

Plants of the new Rose can be compared to plants of the Rose 'QIR 1631', disclosed in a U.S. Plant Patent application filed concurrently. In side-by-side comparisons, plants of the new Rose differ primarily from plants of 'QIR 1631' in flower color as plants of 'QIR 1631' have red purple-colored flowers.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph on the first sheet comprises a side perspective view of a typical plant of 'QIR 1601' grown in a container.

The photograph on the second sheet is a close-up view of a typical open flower of 'QIR 1601'.

The photograph at the top of the third sheet is a close-up view of the upper and lower surfaces of typical flowers of 'QIR 1601'.

The photograph at the bottom of the third sheet is a close-up view of the upper and lower surfaces of typical leaves of 'QIR 1601'.

DETAILED BOTANICAL DESCRIPTION

Plants of the new Rose have not been observed under all possible combinations of environmental conditions and cultural practices. The phenotype may vary somewhat with variations in environmental conditions such as temperature and light intensity, without, however, any variance in genotype. The aforementioned photographs, following observations and measurements describe plants grown during the autumn in a glass-covered greenhouse in Odense, Denmark and under cultural practices typical of commercial potted Rose production. Plants were grown in 13-cm containers, pinched one time and were three months old when the photographs and description were taken. During the production of the plants, day and night temperatures averaged 21° C. and light levels ranged from 60 to 100 klux. In the following description, color references are made to The Royal Horticultural Society Colour Chart, 2001 Edition, except where general terms of ordinary dictionary significance are used.

Botanical classification: *Rosa hybrida* 'QIR 1601'.

Parentage:

*Female, or seed, parent.*—*Rosa hybrida* 'Sunbeam', not patented.

*Male, or pollen, parent.*—Proprietary selection of *Rosa hybrida* identified as code number 243, not patented.

Propagation:

*Type.*—By cuttings.

*Time to produce a rooted young plant, summer.*—About 24 days at soil temperatures about 23° C.

*Time to produce a rooted young plant, winter.*—About 24 days at soil temperatures about 21° C.

*Root description.*—Fibrous, fine; close to 158B in color.

*Rooting habit.*—Freely branching; medium density.

Plant description:

*Plant and growth habit.*—Upright and mounding plant habit; moderately vigorous growth habit; freely branching habit, pinching enhances lateral branch development; dense and bushy appearance.

*Plant height.*—About 25 cm to 30 cm.

*Plant width* (*spread*).—About 20 cm to 25 cm.

*Lateral branches.*—Length: About 12 cm to 18 cm. Diameter: About 3 mm to 5 mm. Internode length: About 1 cm to 3 cm. Strength: Strong. Texture: Smooth, glabrous. Color: Close to 138A. Thorns: Density: About two to five per linear centimeter. Shape: Acicular with subulate apices. Height: About 5 mm to 10 mm. Diameter, at base: About 2 mm to 4 mm. Color, immature: Close to 161A. Color, mature: Close to 166B.

Leaf description:

*Arrangement.*—Alternate; compound with five or seven leaflets per leaf.

*Leaf length.*—About 6 cm to 8 cm.

*Leaf width.*—About 5 cm to 7 cm.

*Terminal leaflet length.*—About 3.5 cm to 5 cm.

*Terminal leaflet width.*—About 1.5 cm to 2.5 cm.

*Lateral leaflet length.*—About 2.5 cm to 3.5 cm.

*Lateral leaflet width.*—About 1.5 cm to 2 cm.

*Leaflet shape.*—Ovate.

*Leaflet apex.*—Acute.

*Leaflet base.*—Obtuse.

*Leaflet margin.*—Serrate.

*Leaflet texture, upper and lower surfaces.*—Smooth, glabrous; somewhat leathery.

*Leaflet venation pattern.*—Pinnate; reticulate.

*Leaflet color.*—Developing leaflets, upper surface: Close to 146A. Developing leaflets, lower surface: Close to 174A. Fully developed, upper surface: Close to 139A; venation, close to 137A. Fully developed, lower surface: Close to N138A and 176B; venation, close to 138A.

*Petioles.*—Leaf petiole length: About 1.5 cm to 2 cm. Leaf petiole diameter: About 2 mm to 5 mm. Leaflet petiole length: About 1 mm to 2 mm. Leaflet petiole diameter: About 1 mm. Leaf petiole texture, upper and lower surfaces: Smooth, glabrous. Leaflet petiole texture, upper and lower surfaces: Smooth, glabrous. Leaf petiole color: Upper surface: Close to 139A. Lower surface: Close to 138A. Leaflet petiole color: Upper surface: Close to 138A. Lower surface: Close to 138B.

*Leaf stipules.*—Quantity: Two per leaf. Length: About 7 mm to 20 mm. Width: About 1 mm. Shape: Subulate. Apex: Acuminate. Base: Truncate; sessile. Margin: Dentate. Texture, upper and lower surfaces: Smooth, glabrous. Color, upper surface: Close to 139B. Color, lower surface: Close to 139C.

Flower description:

*Flower type and habit.*—Large double flowers with numerous petaloids; consistently symmetrical rosette flowers; flowers borne on strong and erect peduncles with one terminal flower per lateral branch; flowers face upright.

*Flowering season.*—Year-round under greenhouse conditions, optimal flowering from spring through autumn under garden conditions; plants begin flowering about five to seven weeks after planting.

*Post-production longevity.*—Good postproduction longevity, plants maintain good substance for about seven to nine weeks; flowers persistent.

*Fragrance.*—Moderately fragrant; pleasant.

*Flower diameter.*—About 4 cm to 5 cm.

*Flower depth* (*height*).—About 2 cm to 3 cm.

*Flower buds.*—Length: About 1.5 cm to 2 cm. Diameter: About 1 cm to 1.5 cm. Shape: Ovoid. Color: Close to 8A.

*Petals.*—Quantity: About five to seven in a single whorl; petals imbricate. Length: About 2 cm to 3 cm. Width: About 2 cm to 2.5 cm. Shape: Obovate. Apex: Acuminate. Base: Attenuate. Margin: Entire. Texture, upper and lower surfaces: Smooth, glabrous; velvety. Color: When opening, upper surface: Close to 7A. When opening, lower surface: Close to 6A. Fully opened, upper surface: Close to 4A; color becoming closer to 9B with development. Fully opened, lower surface: Close to 6C.

*Petaloids.*—Quantity: About 50 to 100 arranged in numerous whorls; petaloids imbricate. Length: About 1 cm to 2 cm. Width: About 1 cm to 1.5 cm. Shape: Obovate. Apex: Acuminate. Base: Attenuate. Margin: Entire. Texture, upper and lower surfaces: Smooth, glabrous; velvety. Color: When opening, upper and lower surfaces: Close to 13A. Fully opened, upper and lower surfaces: Close to 11A.

*Sepals.*—Quantity and arrangement: Typically five in a single star-shaped whorl. Length: About 2 cm to 3 cm. Width: About 5 mm to 10 mm. Shape: Lanceolate. Apex: Acuminate. Base: Obtuse. Margin: Mostly entire with sepal appendages of varying number, size and shape. Texture, upper and lower surfaces: Fine pubescence. Color: When opening, upper surface: Close to 137B. When opening, lower surface: Close to 148C. Fully opened, upper surface: Close to 137B. Fully opened, lower surface: Close to 147C.

*Peduncles*.—Length: About 5 mm to 15 mm. Diameter: About 3 mm. Strength: Strong. Aspect: Erect. Texture: Smooth, glabrous. Color: Close to 144A.

*Reproductive organs*.—Stamens: Quantity per flower: About 20 to 50. Anther length: About 2 mm to 3 mm. Anther shape: Lanceolate. Anther color: Close to 14A. Filament color: Close to 12D. Pollen amount: Scarce. Pollen color: Close to 14B. Pistils: Quantity per flower: About 50 to 100. Pistil length: About 5 mm to 10 mm. Stigma shape: Round. Stigma color: Close to 163A. Style length: About 5 mm. Style color: Close to 157A; distally, close to N34A. Receptacle height: About 5 mm to 10 mm. Receptacle diameter: About 5 mm to 10 mm. Receptacle shape: Cup-shaped. Receptacle texture: Smooth, glabrous. Receptacle color: Close to 144A. Fruits: Quantity per flower: One. Length: About 1 cm to 2 cm. Diameter: About 1.2 cm to 2.2 cm. Texture: Smooth, glabrous. Color: Close to 42B and 26A. Seeds: Quantity per fruit: About six to eight. Length: About 3 mm to 5 mm. Diameter: About 2 mm to 4 mm. Texture: Smooth, glabrous. Color: Close to 166B, 166C and 165C.

Pathogen & pest resistance: Plants of the new Rose have not been observed to be resistant to pathogens and pests common to Rose plants.

Temperature tolerance: Plants of the new Rose have been observed to tolerate temperatures ranging from about 3° C. to about 35° C. to 40° C.

It is claimed:

1. A new and distinct Rose plant named 'QIR 1601' as illustrated and described.

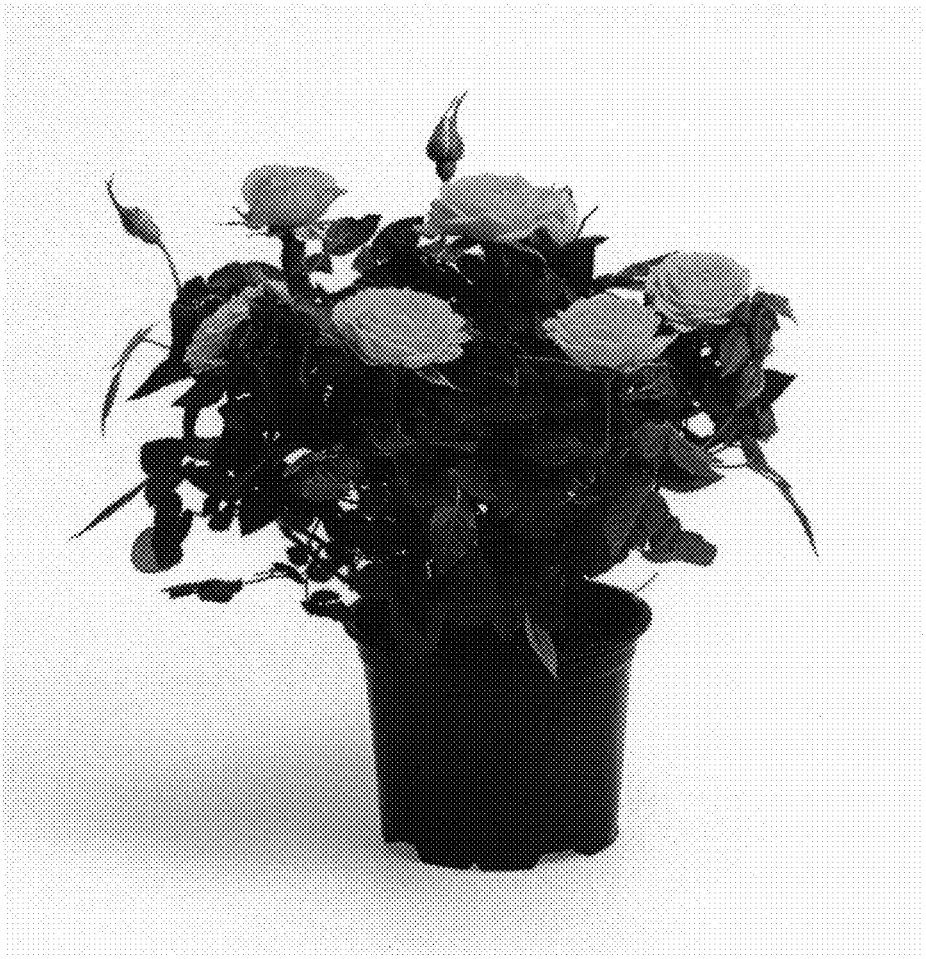

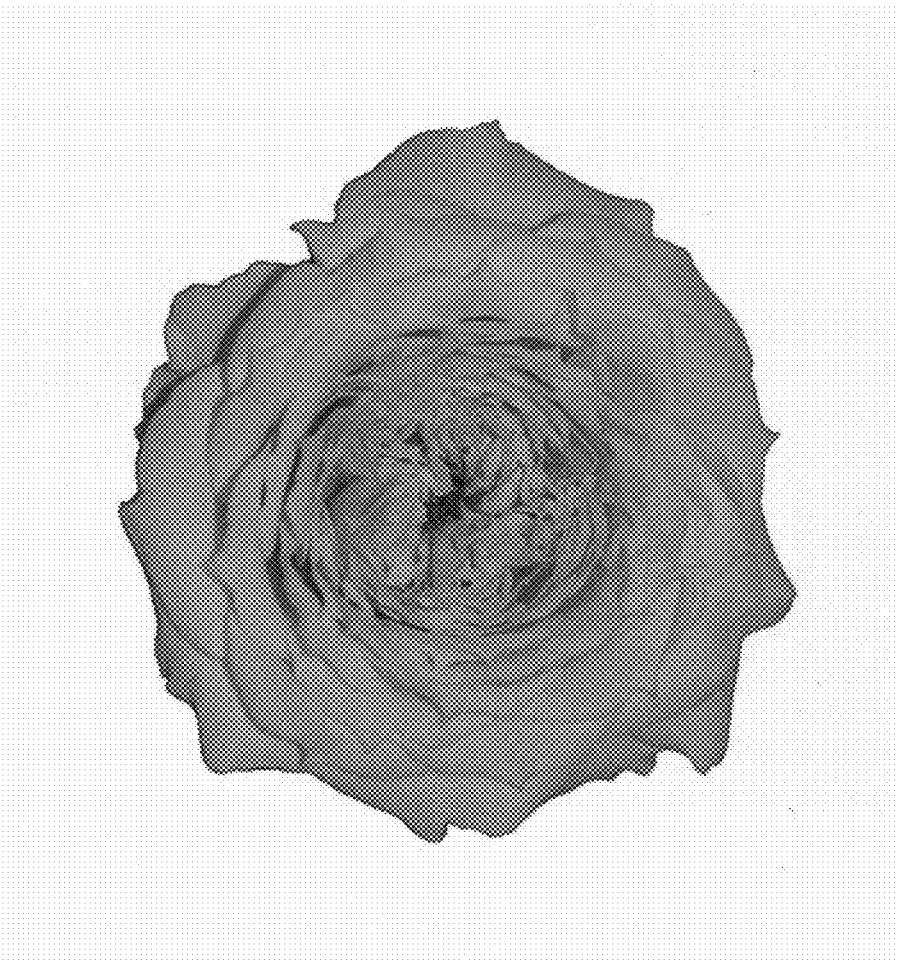

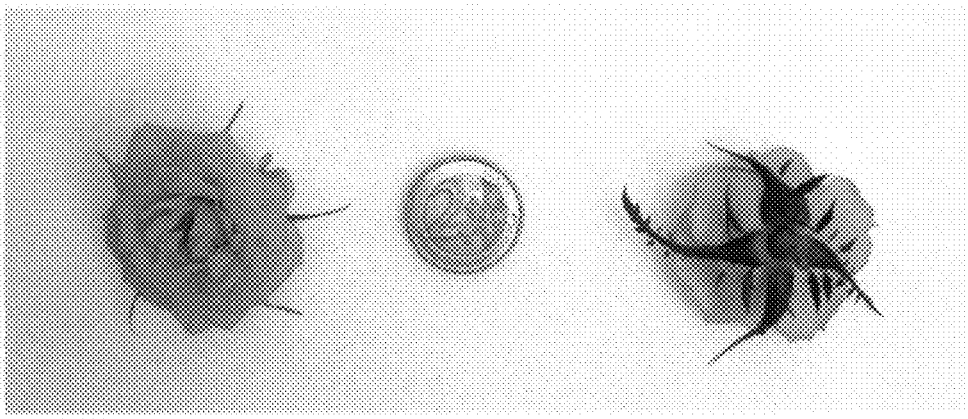
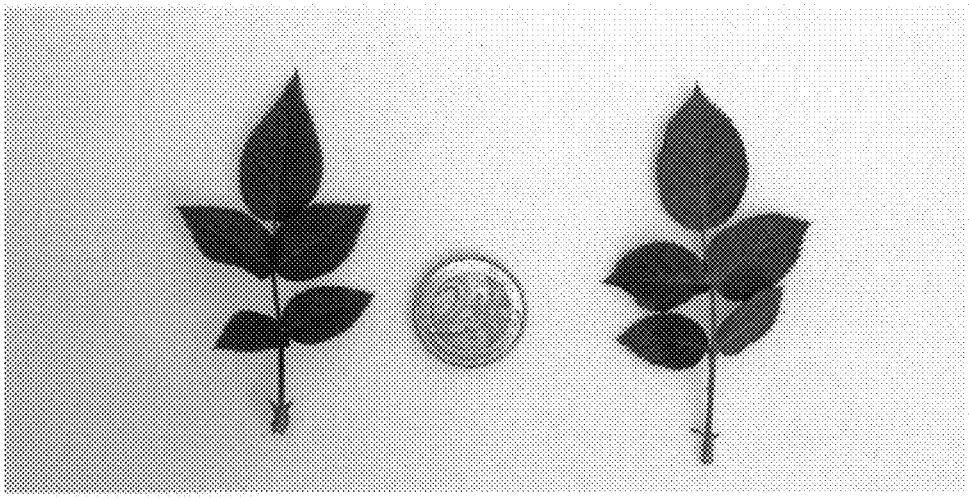

* * * * *